US009835547B2

(12) United States Patent
Manning et al.

(10) Patent No.: US 9,835,547 B2
(45) Date of Patent: Dec. 5, 2017

(54) METHOD AND AN APPARATUS FOR IDENTIFYING A CONTENT PROPERTY OF FOODSTUFF

(71) Applicant: SensAbility Pty Ltd, Glenalta (AU)

(72) Inventors: Sean Manning, O'Halloran Hill (AU); Kristopher John Rowland, Glenalta (AU); Andrew Callum Richardson, Kent Town (AU)

(73) Assignee: SensAbility Pty Ltd, Adelaide (AU)

( * ) Notice: Subject to any disclaimer, the term of this patent is extended or adjusted under 35 U.S.C. 154(b) by 0 days.

(21) Appl. No.: 15/069,896

(22) Filed: Mar. 14, 2016

(65) Prior Publication Data

US 2016/0195469 A1    Jul. 7, 2016

Related U.S. Application Data (63) Continuation of application No. PCT/AU2014/000941, filed on Sep. 26, 2014.

(30) Foreign Application Priority Data

Sep. 27, 2013 (AU) .............................. 2013903741

(51) Int. Cl.
*G01N 21/25* (2006.01)
*A47J 37/08* (2006.01)
(Continued)

(52) U.S. Cl.
CPC .............. *G01N 21/251* (2013.01); *A23L 5/15* (2016.08); *A47J 37/08* (2013.01); *A47J 37/085* (2013.01);
(Continued)

(58) Field of Classification Search
CPC .................................................. G01N 21/251
(Continued)

(56) References Cited

U.S. PATENT DOCUMENTS 6,011,242 A * 1/2000 Westerberg ............. A47J 27/62
219/411
6,845,326 B1 * 1/2005 Panigrahi .................. G01J 3/02
250/339.02
(Continued)

FOREIGN PATENT DOCUMENTS

GB           2098725 A     11/1982
GB           2199733 A      7/1988
(Continued)

OTHER PUBLICATIONS

International Search Report dated Apr. 2, 2015 in PCT Application No. PCT/AU2014/000941, 4 pages.
(Continued)

*Primary Examiner* — Tarifur Chowdhury
*Assistant Examiner* — Omar Nixon
(74) *Attorney, Agent, or Firm* — Kilpatrick Townsend & Stockton LLP (57) ABSTRACT

The present invention relate to an apparatus for processing of foodstuff. The apparatus comprises an element for processing of the foodstuff. The apparatus further comprises a light source that is arranged to emit light having at least two wavelengths or wavelength ranges, the light source further being arranged to direct the light to a surface of at least the foodstuff, and a detector positioned to detect at least a portion of light reflected from the surface of the foodstuff, and arranged to generate an output indicative of the detected intensity. In addition, the apparatus comprises a component for identifying a content property of the foodstuff, the component being arranged to determine a relation between a generated output for one of the at least two wavelengths or wavelength ranges and a generated output for the other or another one of the at least two wavelengths or wavelength ranges, the component further being arranged to compare the determined relation with predetermined data to generate information indicative of the content property of the foodstuff. The apparatus is arranged such that processing of the
(Continued)

foodstuff is controlled using the information indicative of the content property of the foodstuff.

20 Claims, 3 Drawing Sheets (51) Int. Cl.
*G01N 21/27* (2006.01)
*G01N 33/10* (2006.01)
*A23L 5/10* (2016.01)

(52) U.S. Cl.
CPC ............. *G01N 21/25* (2013.01); *G01N 21/27* (2013.01); *G01N 33/10* (2013.01); *A23V 2002/00* (2013.01); *G01N 2201/062* (2013.01)

(58) Field of Classification Search
USPC ........................................................ 356/445
See application file for complete search history.

(56) References Cited

U.S. PATENT DOCUMENTS

| 2006/0098211 | A1* | 5/2006 | Merkel | ............... | G01N 22/04 356/601 |
| 2006/0115559 | A1* | 6/2006 | Jones, Jr. | ............... | A22B 5/007 426/231 |
| 2008/0141867 | A1* | 6/2008 | Cavada | .................... | F24C 7/08 99/332 |
| 2011/0002677 | A1* | 1/2011 | Cochran | .............. | H05B 3/0057 392/416 |
| 2012/0074047 | A1* | 3/2012 | Deefholts | .............. | B07C 5/342 209/587 |
| 2013/0208285 | A1* | 8/2013 | Miettinen | ............ | G01N 21/251 356/600 |

FOREIGN PATENT DOCUMENTS

| GB | 2461092 A | 12/2009 |
| JP | 2004084992 A | 3/2004 |
| JP | 2007263583 A | 10/2007 |
| WO | 2002060302 A2 | 8/2002 |
| WO | 2014053002 A2 | 4/2014 |

OTHER PUBLICATIONS

Extended European Search Report dated Mar. 17, 2017 in EP Patent Application No. 14850059.8. 8 pages.

* cited by examiner

METHOD AND AN APPARATUS FOR IDENTIFYING A CONTENT PROPERTY OF FOODSTUFF

CROSS-REFERENCES TO RELATED APPLICATIONS

This application is a continuation application of PCT application PCT/AU2014/000941 entitled "A METHOD AND AN APPARATUS FOR IDENTIFYING A CONTENT PROPERTY OF FOODSTUFF," filed on Sep. 26, 2014, which claims priority to Australian Patent Application No. 2013903741, filed on Sep. 27, 2013, which are herein incorporated by reference in their entirety for all purposes.

FIELD OF THE INVENTION

The present invention relates to an apparatus and method for identifying a content property of foodstuff.

BACKGROUND OF THE INVENTION

A conventional toaster has a timer used to set the time for toasting one or more slices of bread. However, the optimal toasting time is dependent on a number of factors. For example, the toasting time for a desired brownness of bread depends on the type of the bread (white bread, rye bread, whole meal bread etc.) and other factors such as sugar content and the state of the bread (frozen, stale, etc.). Thus, it is difficult to select the optimal time for toasting and browning the bread.

BRIEF SUMMARY OF THE INVENTION

In accordance with a first aspect of the present invention, there is provided an apparatus for processing of foodstuff, the apparatus comprising:

an element for processing the foodstuff;

a light source for emitting light having at least two wavelengths or wavelength ranges, the light source further being arranged to direct the light to a surface of at least the foodstuff; and a detector positioned to detect at least a portion of light reflected from the surface of the foodstuff, and arranged to generate an output indicative of the detected intensity;

wherein the apparatus is arranged to determine a relation between a generated output for one of the at least two wavelengths or wavelength ranges and a generated output for the other or another one of the at least two wavelengths or wavelength ranges, the apparatus further being arranged to compare the relation with predetermined data such that a content property of the foodstuff can be identified; and wherein the apparatus is arranged to control the element for processing the foodstuff using information associated with the identified content property of the foodstuff.

For the ease of understanding, the term "light" is used throughout the patent specification as a synonym for electromagnetic radiation which may include visible light and also invisible light.

In some embodiments, the foodstuff is breadstuff, such as bread, bagel, pretzel, biscuits, cookies or the like.

The content property of the foodstuff may be a type of the foodstuff. In embodiments in which the foodstuff is breadstuff, exemplary types of breadstuff may include white bread, brown bread, rye bread, wholemeal bread, bagel, pretzel and any other suitable type of breadstuff. However, a person skilled in the art will appreciate that other suitable content properties are envisaged such as moisture content or sugar content. The moisture content may for example be indicative of a state of the foodstuff (frozen, fresh, etc.).

In an embodiment, the apparatus comprises a component for identifying the content property of the foodstuff wherein the component is arranged to determine the relation and to compare the relation with the predetermined data such that the content property of the foodstuff can be identified.

In an embodiment, the information associated with the content property of the foodstuff comprises a processing parameter, wherein the processing of the foodstuff is dependent on at least the processing parameter. The processing parameter may for example be a rate and/or a time period of processing of the foodstuff. Thus, the apparatus may be arranged to control a rate and/or a time period of processing of the foodstuff such as a rate of a change of the chromatic property of the foodstuff. The apparatus may also be arranged to end or interrupt processing such as a change in the chromatic property of the foodstuff. For example, the apparatus may be arranged to deactivate the element for processing of the foodstuff. If the apparatus comprises a plurality of elements for processing of the foodstuff, the apparatus may control a number of the elements that is activated for processing of the foodstuff.

In a specific embodiment, the apparatus comprises a controller for controlling the element for processing the foodstuff.

In some embodiments, the apparatus is arranged to effect a change of a chromatic property of a surface of the foodstuff. Specifically, the apparatus may be arranged to effect a change of colour of the surface of the foodstuff. More specifically, the apparatus may be arranged for browning foodstuff.

In one embodiment, the apparatus comprises an interface and the apparatus is arranged to facilitate selection by a user of a desired outcome of the processing of the foodstuff using the interface. In this regard, the apparatus is arranged such that the processing of the foodstuff results in the selected desired outcome. Specifically, the apparatus may be arranged such that the processing of the foodstuff is controlled using the information associated with the content property and the selected desired outcome. For example, the desired outcome may be indicative of a desired brownness of a surface of the bread.

In addition, the apparatus may further be arranged to facilitate selection of a user profile by the user using the interface. Specifically, the apparatus may comprise a storage device for collecting and storing data indicative of user profiles. A user profile may comprise user preference data such as information indicative of a desired brownness of the bread associated with at least one identified type of bread. In an example, the preference data may further comprise point of times in a day, week, month or year at which the user tends to use the toasting appliance for browning a particular type of bread. The apparatus may be arranged such that when a user selects a user profile, the processing of the foodstuff is controlled using the preference data associated with the selected user profile. A user profile may further comprise an identification of the user such as a name or information indicative of the user such as a fingerprint.

In a specific embodiment, the interface is implemented using a touch sensitive screen.

The interface may further be arranged to communicate at least the identified content property of the foodstuff to a user. For example, the identified content property of the foodstuff may be communicated directly or indirectly by virtue of an audio signal or a visual signal. For example, information indicative of the content property may be displayed on a display. In this regard, the interface may be implemented using a touch sensitive display.

In addition to information indicative of the identified content property, the interface may be arranged to communicate a progress of the processing of the foodstuff such as the change of the chromatic property.

In an embodiment, the interface comprises a network interface arranged to enable communication of information via a communications network such as a local area network, mesh network, the Internet or a peer-to-peer network.

For example, the information indicative of the identified content property and/or a progress of the processing of the foodstuff may be communicated to a handheld unit for example in a wireless manner. In addition, the apparatus may be arranged to receive an input indicative of the desired outcome from the handheld unit. In a specific embodiment, the hand held unit is a mobile device such as a mobile phone or a tablet.

The determined relation may be a ratio, a difference, a combination of the aforementioned or any other suitable relation such as a polynomial, logarithmic or exponential relation. Specifically, in one embodiment the relation is a normalised difference that may be defined as a difference of the information for one of the at least two wavelengths or wavelength ranges and the other or another of the at least two wavelengths or wavelength ranges over a sum of the information for one of the at least two wavelengths or wavelength ranges and for the other or another of the at least two wavelength or wavelength ranges.

In some embodiments, the predetermined data comprises a plurality of predetermined relations, each predetermined relation being associated with at least one content property of the foodstuff, such as a type of breadstuff. Thus, by comparing the determined relation with the predetermined data, at least one content property of the foodstuff can be identified, such as the type of breadstuff.

In a specific embodiment, the apparatus may further be arranged to compare information for at least one of the at least two wavelengths or wavelength ranges with the predetermined data. In this case, the predetermined data also comprises predetermined values that are indicative of the reflected intensity of the at least one of the at least two wavelengths or wavelength ranges. Each predetermined value is associated with a content property of the foodstuff such as a type of the foodstuff. This may be particularly advantageous if the determined relation is associated with more than one content property. For example, a determined relation may be associated with two types of breadstuff. By comparing a further variable to the predetermined data, the type of the breadstuff may be unambiguously identified.

The apparatus may be a suitable heating apparatus such as an electric appliance or a gas operated appliance. For example, the apparatus may be a toasting appliance for breadstuff, a solar oven or a roasting appliance for coffee beans.

The element for processing the foodstuff may comprise a heating source that is arranged to effect a change of chromatic property of the surface of the foodstuff. For example, the source may comprise a heating element. Alternatively, the source may for example be provided in the form of an oven cavity.

In one embodiment, the light source comprises at least two component light sources that are arranged to emit light having the respective wavelengths or wavelength ranges. For example, the light source may comprise at least two light emitting diodes ("LEDs") that emit light having the respective wavelengths or wavelength ranges. The light source may be arranged such that the foodstuff is illuminated with light generated by a first component light source and light generated by a second component light source in sequence. Alternatively, the at least two component light sources may be arranged to illuminate the foodstuff simultaneously. The detector may comprise at least one respective detector element for each component light source.

In an alternative embodiment, the light source is a broadband light source, such as a single broadband light source that is arranged to emit the light having the at least two wavelengths or wavelength ranges.

The apparatus may comprise at least one filter that is arranged to filter the light such that the detector detects light having the respective wavelength ranges or wavelengths in sequence. In one specific example, the apparatus comprises at least two filters that are arranged to filter the light to provide light having the respective wavelength or wavelength ranges.

The first wavelength or wavelength range may be selected in a manner such that the intensity of light reflected from the foodstuff and having the first wavelength or wavelength range is dependent on the chromatic property. For example, the first wavelength range may include the range of 450 nm-500 nm, 500 nm-550 nm, 550 nm-600 nm, 650 nm-700 nm, 750 nm-800 nm or even higher and the first wavelength may be a wavelength within any one of these ranges. In a specific example, the wavelength range may be selected based on the full-width at half maximum of the light intensity emitted by the light source.

The second wavelength or wavelength range typically is selected such that the intensity of the reflected portion of light having the second wavelength or wavelength range is less dependent on the chromatic property than the reflected light having the first wavelength or wavelength range. In one specific example, the reflected intensity of light having the second wavelength or wavelength range is largely independent from a change in the chromatic property.

The second wavelength range may be within any suitable wavelength range including for example the visible, near infrared or infrared range. For example, the second wavelength range may include the range of 800 nm-1800 nm, 800 nm-1400 nm, 850 nm-1150 nm, or 850 nm-950 nm and the second wavelength may be a wavelength within any one of these ranges. For example, the second wavelength range may be within approximately 750 nm to 1400 nm.

The detector may further be arranged to detect a background light when the light source does not emit the light having the at least two wavelengths or wavelength ranges, and provide information indicative of the intensity of the background light for the receiving portion. The background light may for example be ambient light from a heating element, ambient room light, or light from any other source. In one embodiment, the determiner may further be arranged to correct the information and/or the determined relation using the information indicative of the intensity of the background light.

In one embodiment, the detector is positioned to detect reflected light exclusively from the surface of the foodstuff. The detector typically comprises a single detector element, but may alternatively also comprise more than one detector element, such as two detector elements that are arranged to detect portions of reflected light from the surface of the foodstuff. For example, the detector may comprise a detector element for each light source component.

The apparatus may also be arranged to determine whether the foodstuff is present or absent. For example, if the foodstuff is absent, the apparatus may receive information indicative of an intensity of light that is reflected from a surface of the apparatus. Further, if it is determined that the foodstuff is absent, the apparatus may be arranged to deactivate the element for processing the foodstuff and/or generate an alert signal.

In an embodiment, the apparatus may be arranged to deactivate the element for processing the foodstuff and/or generate an alert signal if no reflected light is detected by the detector. This may be indicative of a malfunction of a component of the apparatus.

In accordance with a second aspect of the present invention, there is provided a device for identifying a content property of foodstuff, the device comprising:

a light source for emitting light having at least two wavelengths or wavelength ranges; and a detector arranged to generate an output indicative of a detected intensity;

wherein when light from the light source is directed to a surface of at least the foodstuff, at least a portion of light reflected from the surface of the foodstuff is detected by the detector and outputs are generated indicative of the detected intensity by the detector, the device is arranged to determine a relation between a generated output for one of the at least two wavelengths or wavelength ranges and a generated output for the other or another one of the at least two wavelengths or wavelength ranges, and wherein the device is further arranged to compare the relation with predetermined data such that a content property of the foodstuff can be identified.

In an embodiment, information associated with the identified content property of the foodstuff is used for controlling an element arranged for processing foodstuff, such as a heating element.

In an embodiment, the device is a handheld device.

In accordance with a third aspect of the invention, there is provided a method of identifying a content property of foodstuff, the method comprising the steps of:

providing the foodstuff having a surface;

illuminating the surface of the foodstuff with light having at least two wavelengths or wavelength ranges;

detecting at least a portion of light that is reflected and generating information indicative of an intensity of the detected reflected light for the at least two wavelength or wavelength ranges;

determining a relation between information for one of the at least two wavelengths or wavelength ranges and information for the other or another one of the at least two wavelengths or wavelength ranges;

comparing the determined relation to predetermined data such that a content property of the foodstuff can be identified;

processing the foodstuff; and controlling the processing of the foodstuff using at least information associated with the identified content property of the foodstuff.

The step of processing the foodstuff may comprise effecting a change of a chromatic property of a surface of the foodstuff. For example, effecting a change of a chromatic property may comprise exposing the surface of the foodstuff to a heating source.

In an embodiment, the information associated with the content property comprises a processing parameter.

The step of controlling the processing of the foodstuff may comprise controlling a processing parameter that affects the processing of the foodstuff. Exemplary processing parameters may include a rate of the processing of the foodstuff and a duration of the processing of the foodstuff. Additionally or alternatively, if the heating source comprises a plurality of heating elements, the step of controlling the processing of the foodstuff may comprise controlling a number of the heating elements that is activated to effect the change of the chromatic property of the surface of the foodstuff.

Determining the relation may comprise determining a ratio, a difference, a combination of the aforementioned or any other suitable relation such as a logarithmic or exponential relation. In one specific embodiment, the relation is a normalised difference that may be defined as a difference of the information for one of the at least two wavelengths or wavelength ranges and the other or another of the at least two wavelengths or wavelength ranges over a sum of the information for one of the at least two wavelengths or wavelength ranges and the other or another of the at least two wavelength or wavelength ranges.

In one embodiment, the method may comprise a step of comparing the information for one of the at least two wavelengths or wavelength ranges to the predetermined data. In this way, the content property may be unambiguously identified.

The content property of the foodstuff may be identified prior to effecting the processing of the foodstuff. The processing may comprise effecting a chromatic change of a surface of the foodstuff which may comprise exposing the surface of the foodstuff to a heating source. The source may, for example, comprise a heating element.

Alternatively, the content property of the foodstuff may be identified at least partially during the step of effecting the processing of the foodstuff.

The method may comprise facilitating selection of a desired outcome of the processing of the foodstuff by a user, and the step of effecting the processing may be conducted such that the processing of the foodstuff results in the desired outcome. Further, the step of controlling the processing may comprise using at least the information associated with the identified content type of foodstuff and the selected desired outcome.

The method may further comprise a step of facilitating selection of a user profile by a user.

In this regard, the method may comprise collecting and storing data indicative of user profiles, each user profile may comprise a desired outcome associated with a content property of the foodstuff. The method may be conducted such that when a user selects a user profile, the step of controlling the processing is conducted automatically using information associated with the selected user profile.

The method may further comprise a step of detecting a background light when the surface of the foodstuff is not illuminated with the light having the at least two wavelengths or wavelength ranges, and a step of receiving information indicative of the intensity of the background light. Additionally, the method may comprise a step of correcting the information for the at least two wavelength or wavelength ranges and/or the determined relation using the provided information indicative of the intensity of the background light.

BRIEF DESCRIPTION OF THE DRAWINGS

The present invention will now be described, by way of example only, with reference to the accompanying drawings, in which.

DETAILED DESCRIPTION OF THE INVENTION

In a generic form, embodiments of the present invention relate to an apparatus for processing of foodstuff. The apparatus comprises an element for processing the foodstuff. The apparatus is arranged to identify a content property of the foodstuff and to control the processing of the foodstuff by using information associated with the identified content property of the foodstuff.

The optimal processing of foodstuff is dependent on a number of factors such as the type of the foodstuff or any other suitable content property of the foodstuff, such as moisture content or sugar content. As such, it is desirable to identify at least one content property of the foodstuff in order to improve the processing of the foodstuff In some embodiments, the processing of the foodstuff results in a change in a chromatic property of at least a surface of the foodstuff. For example, if the foodstuff is breadstuff, the change of the chromatic property may be a change of brownness ("browning") of the surface of the breadstuff. The browning of the surface of breadstuff is dependent on a number of content properties of the breadstuff. Such content properties may include a type of the breadstuff, a moisture content that may be indicative of a state of the breadstuff (frozen, fresh, stale, etc.), sugar content of the breadstuff and any other suitable content property that influences the browning of the breadstuff.

Figure 1:
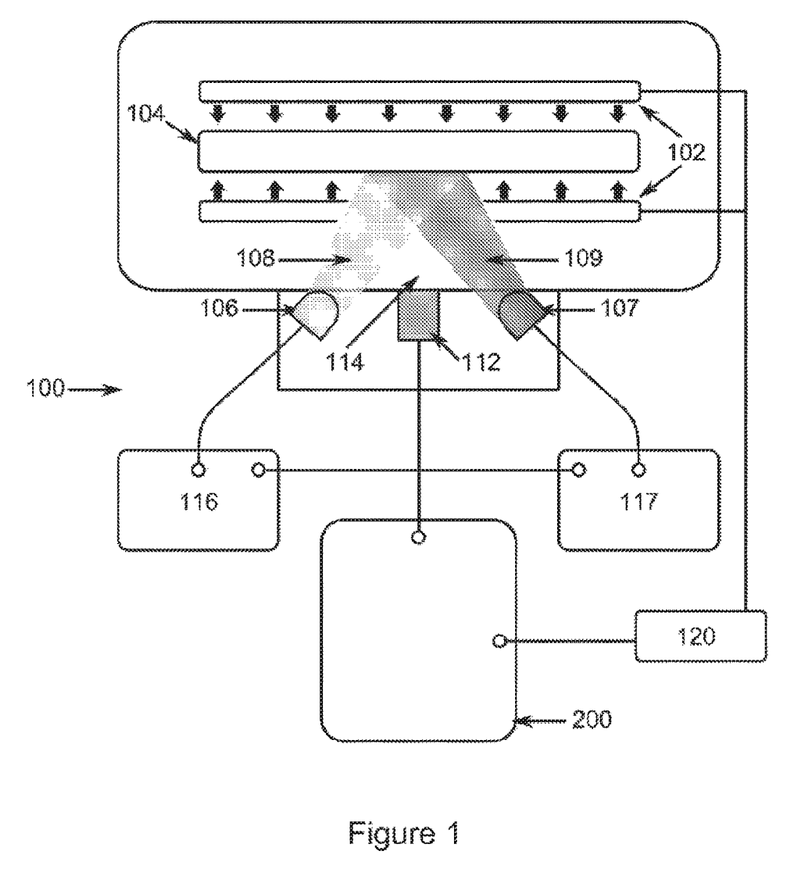
FIG. 1 is a schematic block diagram of components of an apparatus in accordance with an embodiment of the present invention.

Referring now to a specific embodiment of the invention in FIG. 1, there is shown an apparatus 100 for effecting a change of a chromatic property of a surface of the foodstuff. Specifically, the apparatus 100 is a toasting appliance 100 that has a heating element 102 which causes the change of a chromatic property of the surface of the breadstuff. In this case, the chromatic property relates to a brownness of bread 104. In general, browning is caused by processes such as the Maillard reaction or caramelisation. A person skilled in the art will appreciate that the apparatus may be any suitable apparatus that is arranged to process the foodstuff, i.e. effect a change of a chromatic property of the surface of the foodstuff. For example, the apparatus may be an electric or gas-operated appliance. Specifically, the appliance may be arranged to toast breadstuff or to roast coffee beans, or the like.

The toasting appliance 100 comprises a component 200 for identifying a content property of the foodstuff, such as bread 104 that can be positioned within a cavity of the toasting appliance 100. In this specific embodiment, the content property of the foodstuff is a type of the bread 104. Exemplary types of bread may for example include white bread, brown bread, rye bread, wholemeal bread, bagel-type bread or any other suitable type of bread. In this particular example, the component 200 is implemented using a processor.

In this example, the component 200 is incorporated into the toasting appliance 100. However, a person skilled in the art will appreciate that the component 200 may be implemented as a separate device for example in the form of a handheld device.

The toasting appliance 100 is arranged such that the change of brownness of the surface of the bread 104 is controlled using information from the component 200 that is associated with the type of bread 104. In this particular embodiment, the information is indicative of the type of the bread 104. However, the information associated with the type of bread 104 may be a processing parameter that affects the browning of the bread 104.

In this embodiment, the identified type of the bread 104 relates to the initial state of the bread 104 prior to exposing the bread 104 to the heating element 102 that causes the browning process.

The toasting appliance 100 further comprises two light emitting diodes (LEDs) 106 and 107 that emit light 108, 109 having two respective wavelength ranges. The LEDs 106, 107 are arranged to direct the light 108, 109 to an area on the surface of the bread 104 such that a detector 112 (which includes a photo diode) can detect a reflected portion of the light 114. In this and other examples, the LEDs 106, 107 direct the light 108, 109 to the same area on the surface of the bread 104. The area is sufficiently sized such that local variations of the surface of the bread 104 such as grains, raisins, surface shape, surface defects or the like do not substantially affect detection of the reflected portion the light 114 by the detector 112. A suitable spot may have a diameter of approximately 2 cm FWHM in intensity. Further, the area that is detected by the detector is substantially identical to the spot that is illuminated by the LEDs 106, 107. A person skilled in the art will appreciate that the light source may be any suitable light source that emits light having at least two wavelengths or wavelength ranges. For example, the light source may be a broadband light source. Light from the broadband light source may be directed through a filter before reflected by the surface of the foodstuff.

The first wavelength range is typically selected such that the intensity of the reflected portion of light 114 associated with the first wavelength range changes as a function of the brownness of the bread 104. In this particular example, the LED 106 emits light 108 at a signal wavelength $\lambda_1=525$ nm which corresponds to green light. The second wavelength range is typically selected such that the intensity of the reflected portion of light 114 associated with the second wavelength range does not appreciably change as a function of the brownness of the bread 104, in comparison to the first wavelength range. The intensity associated with the second wavelength range provides a reference that does not change appreciably as a function of the brownness of the bread 104. In this particular example, the LED 107 emits light 109 at a reference wavelength $\lambda_2=940$ nm which corresponds to near-infrared light.

A portion of the light 114 that is reflected from the surface of the bread 104 is detected by the detector 112. A person skilled in the art will appreciate that the detector of the apparatus in accordance with embodiments of the invention may comprise one or more detector elements. The detector 112 comprises a photodiode that generates values for the detected reflected light 114 having wavelengths $\lambda_1$ and $\lambda_2$, the generated values are indicative of the intensity of the reflected portion of light 114. In this example, the photodiode of the detector 112 has a peak response at 850 nm and has approximately 60% responsiveness at the wavelengths $\lambda_1=525$ nm and $\lambda_2=940$ nm.

The generated values are then transmitted to the component 200. A person skilled in the art will appreciated that the values for the at least two wavelength could be in the form of any suitable information that is indicative of an intensity of the reflected portion of light 114.

The component 200 is further arranged to determine a relation between the respective values from the detector 112 which are associated with the wavelengths $\lambda_1$ and $\lambda_2$. In this example, the component 200 determines the relation between values associated with the wavelengths $\lambda_1$ and $\lambda_2$ by determining a difference of the values at the wavelengths $\lambda_1$ and $\lambda_2$ over a sum of the values at the wavelengths $\lambda_1$ and $\lambda_2$. This relation may also be referred to as normalised difference. The normalised difference can be determined using the following equation (1):

$$ND = \frac{(I_2 - I_1)}{(I_1 + I_2)} \qquad \text{equation (1)}$$

where ND is the normalised difference, $I_1$ is the value at the wavelength $\lambda_1$ which is indicative of the intensity of the reflected portion of light and $I_2$ is the value at the wavelength $\lambda_2$ which is indicative of the intensity of the reflected portion of light. The normalised difference provides a relative change in the relation that is typically less susceptible to fluctuations in the light sources, e.g., the LEDs or ambient light. Such fluctuations may for example be due to voltage fluctuations, drive current fluctuations or other causes such as gradual decrease in light emission as the LED reaches the end of its lifetime. A person skilled in the art will appreciate that other relations between the two values may be determined such as a difference, a ratio, a combination of a ratio and a difference, a polynomial, logarithmic or exponential relation or any other suitable relation.

Figure 2:
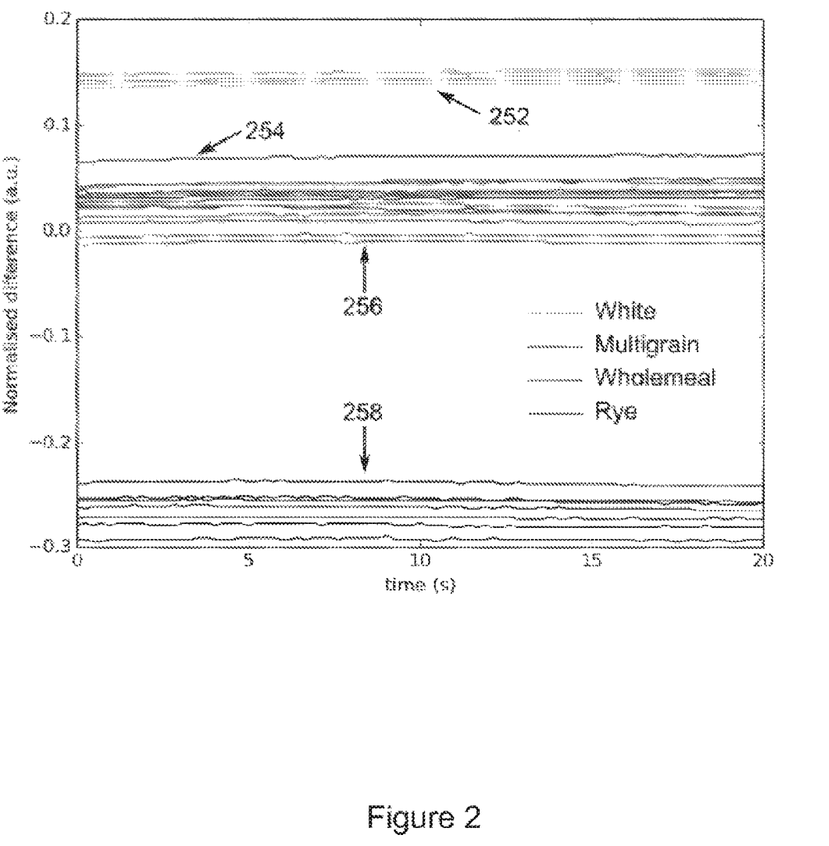
FIG. 2 shows a diagram in which a determined relation is compared for seven samples each of different types of breadstuff.

An example of determined normalised differences for different type of breadstuff using the component 200 is shown in FIG. 2. In particular, FIG. 2 shows a diagram in which the determined normalised difference is illustrated against time for four different types of the bread 104, i.e. white bread, multigrain bread, brown bread and rye bread.

As shown in FIG. 2, the normalised differences for all four types of breadstuff are relatively constant for detection from 0 to 20 seconds. The normalised difference 254 for the multigrain bread and the normalised difference 256 for the wholemeal bread are relatively similar within a range of approximately −0.01 to 0.07. In comparison, the normalised difference 258 for the white bread is in a range of 0.13 to 0.15 and the normalised difference for the rye bread is within a range of −0.24 to −0.3.

For identifying the type of the bread 104, the component 200 is arranged to compare the determined normalised difference with predetermined data that may for example be stored in a storage device (not shown). The predetermined data comprises a plurality of predetermined relations, i.e. normalised differences wherein each of the normalised differences is associated with at least one particular type of bread. For example, the predetermined normalised difference for rye bread may be in a range of −0.2 to −0.4.

The predetermined normalised difference of approximately 0.14 may be associated with white bread and a normalised difference of approximately 0.03 might be associated with multigrain bread and also with wholemeal bread.

In this case, the comparison of the determined normalised difference with predetermined normalised differences may result in more than one type of bread. Thus, a further variable may be necessary to unambiguously identify the type of breadstuff.

In this regard, the component 200 compares at least one of the values $I_1$ and $I_2$ with predetermined data. The predetermined data then also comprises a plurality of values that are indicative of the intensity of the reflected portion of light for the corresponding wavelength associated with a type of foodstuff. For example, the predetermined data may comprise a plurality of types of foodstuff that is associated with a respective range of normalised difference and a range of the value for at least one of the two wavelengths or wavelength ranges. However, a person skilled in the art will appreciate that when the comparison of the determined relation and the predetermined data results in more than one type of bread, the component may be arranged to select one of them without determining a further variable.

As shown in FIG. 2, multigrain bread and wholemeal bread have substantially similar determined normalised differences. Thus, for these two types of bread a further comparison using the values $I_1$ and $I_2$ could be performed. By additionally comparing the intensity values, it could be possible to unambiguously be identified the type of bread.

The component 200 may be implemented using a processor which may also be provided in the form of a suitable integrated chip.

By comparing the determined normalised difference to predetermined data, in some instances it may be possible to not only identify the generic type of bread, but also different brands of breadstuff.

Based on the comparison of the determined relation with the predetermined data, the component 106 generates information indicative of the type of bread 104.

Referring back to FIG. 1, the toasting appliance 100 comprises a controller 120 for controlling the heating element 102. In this embodiment, the controller 120 is incorporated into the toasting appliance 100. For example, the controller 120 may be implemented using a processor. Specifically, both the controller 120 and the component 200 may be implemented using the same processor. A person skilled in the art will appreciate that the controller 120 may be integrated within the component 200 or may be in form of a separate device. The controller 120 is arranged to control the heating element 102 using at least the information indicative of the type of bread 104 that is generated by the component 200. Thus, the change of the brownness is controlled using at least the information indicative of the type of bread 104. Additionally, the controller 120 may control the heating element 102 using a characterised brownness of the bread 104. Details for characterising a chromatic property of foodstuff are disclosed in International patent application No. PCT/AU2013/000809 which is incorporated herein by reference.

In this example, the controller 120 uses the information indicative of the type of bread 104 to control a rate of a change in brownness of the bread 104 and also a duration in which the bread 104 is exposed to heat from the heating element 102. For example, the controller 120 may use the information indicative of the type of the bread to determine the duration and the rate to brown the bread until it reaches a predetermined brownness. A person skilled in the art will appreciate that the controller 120 may further be arranged to end or interrupt the heating element 102, for example, when a desired brownness of the bread 104 has been reached or for safety reasons. As mentioned in the background section, the optimal toasting time to reach a desired brownness of bread is dependent on a range of factors such as the type of bread. Thus, different types of bread may require different durations and/or rates of exposure to the heating element 102 in order to reach a desired degree of brownness.

For example, the information indicative of the identified type of bread may be used to determine a duration for which the bread 104 is exposed to the heating element 102 and/or a rate of heat radiated from the heating element 102.

In this particular example, the toasting appliance 100 further comprises an interface (not shown) arranged to enable communication with a user.

Specifically, the interface is arranged to facilitate selection by a user of a desired brownness of the bread 104. Accordingly, the controller 120 of the toasting appliance 100 controls the heating element 102 using the information indicative of the identified type of the bread 104 and information indicative of the selected desired brownness of the bread 104. The toasting appliance 100 is arranged such that the process of browning of the surface of the bread 104 results in substantially the selected desired brownness. The interface may be provided in form of a touch sensitive screen.

In addition, the interface may be arranged to facilitate selection of a user profile. In this regard, the apparatus comprises a storage device arranged to store data indicative of user profiles. Each user profile may comprise user preference data such as information indicative of a desired brownness associated with a particular type of bread. The information may further be associated with points of time at which a user associated with the user profile tends to use the toasting appliance for browning a particular type of bread. The apparatus may be arranged such that upon selection of a user profile, the apparatus automatically effects the browning of the bread according to the user preference data. The user preference data may further be used to recognise a pattern for a particular user over a period of time. In this way, future behaviour of a user may be predicted via heuristic algorithms or otherwise.

With reference to the interface of the apparatus 100, the interface may comprise a network interface arranged to enable communications of information via a communications network, such as a local area network, mesh network, the Internet or a peer-to-peer network.

For example, the network interface of the toasting appliance 100 may be arranged to communicate information to and/or from a remote handheld unit. Specifically, information indicative of the identified content property may be communicated to the remote handheld unit. In addition, the apparatus may be arranged to receive information from the remote handheld unit via the network interface indicative of a selection of a desired brownness or to control a function of the apparatus. The handheld unit may for example be a mobile phone, a tablet or the like.

In an alternative embodiment, the network interface may be arranged to enable communication between the toasting appliance 100 and a further appliance. For example, the information indicative of the identified type of bread may be used to retrieve information indicative of foodstuff that can be combined with the bread and is stocked in a refrigerator, such as a suitable topping or a beverage. The information retrieved from the refrigerator may subsequently be communicated to the user. In a further example, the toasting appliance 100 may be arranged to activate a further appliance such as a coffee machine. Activation of the further appliance may be automatic or in response to a user input at the interface. In a further example (not shown), the network interface may be arranged to enable communication of suitable information between the toasting appliance 100 and a third party such as bread manufacturers, appliance manufacturers, statistical institutes or the like. The suitable information may for example include user preference data such as a preferred type of bread, a desired brownness of bread, and preferred amounts of toasted bread.

The toasting appliance 100 may further comprise a display which may display suitable information including information indicative of the identified type of bread, the selected desired brownness, and information indicative of a progress of the change in brownness of the bread 104. The suitable information may alternatively be displayed on a display of the handheld unit. In this regard, the interface of the toasting appliance 100 is not only arranged to receive data but also to send data to the handheld unit.

In a specific embodiment, the toasting appliance 100 comprises a touch sensitive display which combines the interface and the display. In this embodiment the touch sensitive display may in use display a scale. The scale represents a plurality of desired brownness' in which a location on the scale is indicative of a desired brownness of the bread. Thus, by touching a location on the displayed scale, the user can select a desired brownness of the bread.

During the browning process of the bread 104, the touch sensitive display may show information indicative of a progress of the browning process for example by virtue of the scale that was displayed for the selection of a desired brownness. Based on the selected desired brownness, the scale may be modified such that the selected desired brownness is associated with 100% of the scale.

A person skilled in the art will appreciate that the information may be displayed in any suitable form such as by virtue of a plurality of LEDs that are arranged to form a progress scale.

With reference to FIG. 2 in which the normalised difference is illustrated against time, it is indicated that the browning process typically is a non-linear process. In other words, during a first period the brownness of the surface of the bread does not significantly change. During a second period, the brownness of the surface of the bread changes in a relatively rapid manner. In one embodiment of the present invention, the display of the toasting appliance is arranged to show information that is indicative of the browning process in a substantially linear manner. For this purpose, the determined relation is modified using a fudge factor. Specifically, during the first period, the display displays information indicative of a linear progress that is irrespective of the actual browning progress and in the second period the display represents information indicative of the actual browning process. As such, even during the first period in which the brownness of the surface of the bread does not significantly change, the display illustrates a progress of browning.

The component 200 of the toasting appliance 100 may further comprise a memory for storing desired outcomes of browning for respective types of breadstuff. The desired outcomes may be associated with pre-set optimal brownness' for respective types of breadstuff. In this case, the user may touch the touch sensitive display once and the toasting apparatus 100 will automatically identify the type of the bread 104 that is within the cavity of the toasting appliance 100. Using information indicative of the identified type of the bread 104, the toasting appliance 100 will subsequently control the heat element 102 so that when the toasting process is completed, the bread 104 is provided in the pre-set optimal brownness for the identified type of bread. This fully automatic process may alternatively be initiated by inserting the bread 104 into the toasting appliance 100.

Additionally or alternatively, the memory may comprise a plurality of desired outcomes indicative of a brownness of bread that can be selected by one or more users. As such, the toasting appliance 100 provides user-specific settings that can be selected using the interface so that the toasting appliance 100 automatically effects a change in brownness that results in the selected user-specific desired brownness for a respective type of bread.

Referring back to FIG. 1, the detector 112 may further detect a background light when the light emitting diodes 106, 107 do not emit any light having the respective wavelength ranges. In this case, the photodiode of the detector 112 further generates a value indicative of the intensity of the background light. The background light may for example be ambient light from a heating element, ambient room light, or light from any other sources being reflected from the bread surface, reflected from other parts of the toaster, or directly illuminating the detector 412.

The component 200 may correct the determined normalised difference by subtracting the detected background light. This may be done using the following equation (2):

$$ND = \frac{(I_2 - I_1)}{(I_1 + I_2 - 2 \times I_0)} \qquad \text{equation (2)}$$

where ND is the normalised difference, $I_1$ is the value at the wavelength $\lambda_1$ which is indicative of the intensity of the reflected portion of light, $I_2$ is the value at the wavelength $\lambda_2$ which is indicative of the intensity of the reflected portion of light and $I_0$ is the value indicative of the intensity of the background light.

A person skilled in the art will appreciate that other suitable arrangements of the apparatus 100 are envisaged. For example, the two LEDs 106 and 107 may emit light concurrently onto the surface of the bread 104 and the at least a portion of reflected light 114 may be detected by sequentially filtering the light before it is detected with a single detector 112.

Alternatively, the detector 112 of the apparatus 100 may comprise more than one detector element, e.g., more than one photodiode. For example, the apparatus may comprise a detector element for each light emitting diode. Further, the apparatus may comprise an additional detector element for detecting the background light. In the case of having more than one detector element, the detector elements may be directed in a substantially similar direction to reduce effects of focussing to a point with a variable sample distance.

In one embodiment (not shown), the toasting apparatus 100 further comprises a sensor for measuring a temperature (not shown). A change in temperature may affect the value generated by the detector of the apparatus, due to the sensitivity of the detector or LED emission spectra being affected. By measuring the temperature, the generated value and/or the determined relation may be corrected.

In a further embodiment (not shown), there is provided a device for identifying a content property of foodstuff, such as a type of breadstuff. This device may be implemented in the form of a handheld device. Similar to the toasting apparatus, the device comprises a light source for emitting light having at least two wavelengths or wavelength ranges, and a detector for generating an output indicative of a light intensity. When light from the light source is directed to a surface of foodstuff such as a slice of bread or cookies, the device is positioned such that at least a portion of light reflected from the surface of the foodstuff is detected by the detector. The detector then generates outputs indicative of the detected intensity. Similar to the component of the toasting appliance, the device is arranged to determine a relation between a generated output for one of the at least two wavelengths or wavelength ranges and a generated output for the other or another one of the at least two wavelengths or wavelength ranges. Furthermore, the device compares the relation with predetermined data such that a content property of the foodstuff can be identified. Information associated with the identified content property of the foodstuff may then be used by an apparatus such as a toasting appliance. However, it is envisaged that the information associated with the identified content property of the foodstuff may be used in an alternative manner. For example, the information may be communicated to a user, stored in a storage device, used for quality control and/or transmitted to a further appliance such as a refrigerator or a coffee machine.

Figure 3:
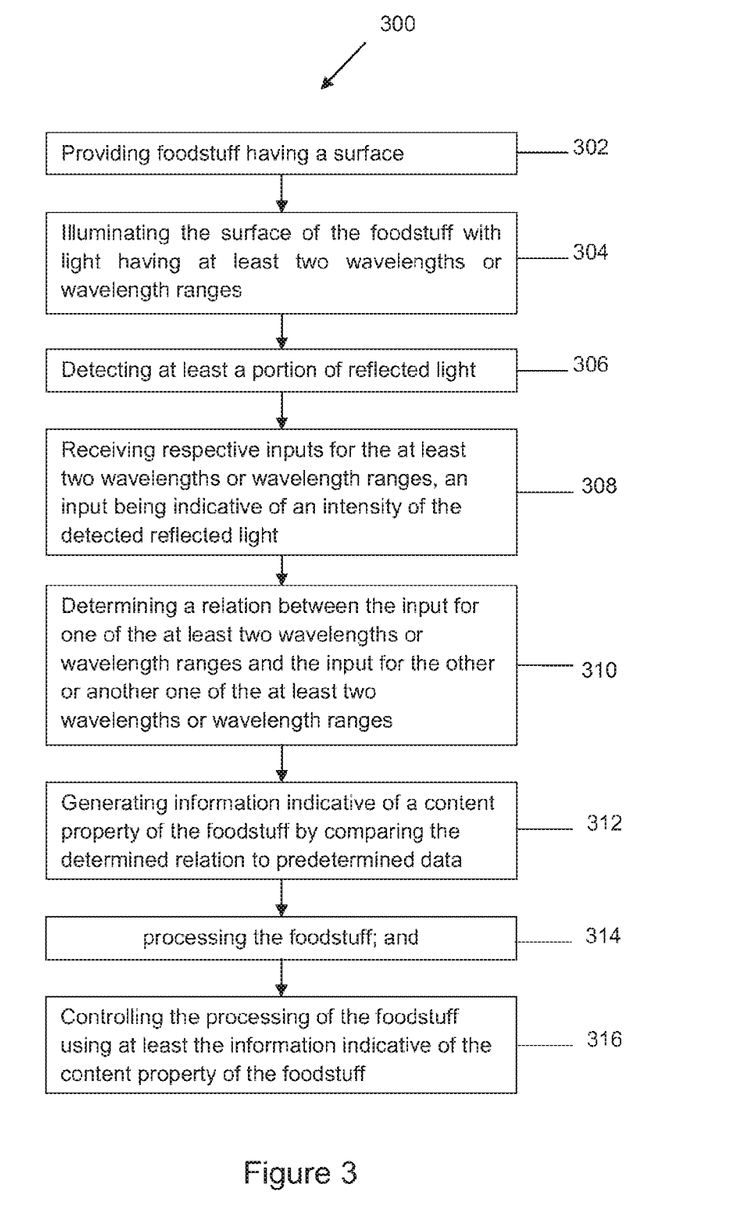
FIG. 3 illustrates a method in accordance with embodiments of the present invention.

Referring now to FIG. 3, a method 300 in accordance with embodiments is illustrated. In a first step 302, a foodstuff is provided having a surface. The surface of the foodstuff is illuminated with suitable light 304 having at least two wavelengths or wavelength ranges. A first wavelength range may be associated with green light and a second wavelength range may be associated with infrared light.

In a further step 306, at least a portion of reflected light is detected and information indicative of an intensity of the reflected portion of light is generated. In the next step 310, a relation is determined between information for one of the at least two wavelengths or wavelength ranges and the other or another of the at least two wavelengths or wavelength ranges. The relation may for example be a normalised difference that is typically defined as a difference divided by a sum. However, any other suitable relation is envisaged. In a further step 312, information is determined that is associated with a content property of the foodstuff such as a type of the foodstuff. For example, the information may be indicative of the content property or indicative of a processing parameter that affects the processing of the foodstuff. The information is determined by comparing the determined relation from the previous step with predetermined data. The predetermined data typically comprises predetermined relations such as normalised differences wherein each predetermined relation is associated with one or more types of foodstuff.

The method 300 further comprises a step 314 of processing of the foodstuff and a step 316 of controlling the processing of the foodstuff using at least the information associated with the content property of the foodstuff. For example, the information may be used to determine a duration of processing of the foodstuff such that the controller activates the element for processing of the foodstuff for the determined duration. The processing may for example be a change of chromatic property such as a change of colour of the surface of the foodstuff.

In an embodiment, the method 300 may comprise a further comparison step. Specifically, the method 300 may comprise a step of comparing information for at least one of the wavelength or wavelength ranges, for example information that is associated with green light, with the predetermined data. For this particular embodiment, the predetermined data also comprises values that are indicative of the reflected intensity for at least one of the wavelengths or wavelength ranges. This may be particularly advantageous if a determined relation is compared and matched with a predetermined relation that is associated with more than one type of foodstuff. By using a further variable, the type of foodstuff may be unambiguously identified.

In one embodiment, the method 300 further comprises facilitating a user to select a desired outcome such as a desired chromatic property of the foodstuff. The step of processing of the foodstuff is then conducted such that the processing results in the selected desired outcome. In this case, the step of controlling the processing is conducted using the information indicative of the identified type of foodstuff and the desired outcome.

Modifications and variations as would be apparent to a skilled addressee are deemed to be within the scope of the present invention. For example, the method 300 may be conducted in an automated manner. Specifically, when a user has selected a desired brownness of the bread, the steps of identifying the type of bread and the step of effecting the change in brownness will be conducted in an automated manner. Further, the apparatus may determine whether foodstuff is present. If the foodstuff is absent, the apparatus may be arranged to receive light that is reflected from a surface of the apparatus. If the apparatus determines that the foodstuff is absent, the apparatus may then deactivate the element for processing of the foodstuff and/or generate an alert signal. The apparatus may also be arranged to deactivate the element for processing of the foodstuff and/or generate an alert signal if no reflected light is received or if light is received that is reflected on a foreign object that is not foodstuff, such as knife or the like.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

What is claimed is:

1. An apparatus for processing of foodstuff, the apparatus comprising:
    an element for processing the foodstuff, the element comprising a source element that is arranged to effect a change of a chromatic property of a surface of the foodstuff;
    a light source for emitting light and positioned to direct the light to the surface of at least the foodstuff, the emitted light having at least two wavelengths or wavelength ranges;
    a light detector positioned to detect at least a portion of the emitted light that is reflected from the surface of the foodstuff, the detector being arranged to generate an output indicative of detected light intensity; and
    a processor for:
        identifying a content property of the foodstuff and being arranged to determine a relation between a generated output for one of the at least two wavelengths or wavelength ranges and a generated output for the other or another one of the at least two wavelengths or wavelength ranges and compare the determined relation with predetermined data such that the content property of the foodstuff can be identified; and
        controlling the element for processing of the foodstuff using information associated with the identified content property of the foodstuff.

2. The apparatus of claim 1 wherein the foodstuff is breadstuff.

3. The apparatus of claim 1 wherein the content property of the foodstuff is indicative of a type of the foodstuff.

4. The apparatus of claim 1, wherein the information associated with the content property of the foodstuff comprises a processing parameter that affects the processing of the foodstuff.

5. The apparatus of claim 4 wherein the processing parameter is a time period for which the foodstuff is processed and/or a rate of processing of the foodstuff.

6. The apparatus of claim 1 comprising an interface that is arranged to facilitate selection of a desired outcome of the processing of the foodstuff, wherein the apparatus is arranged such that the processing of the foodstuff results in the selected outcome.

7. The apparatus of claim 6 wherein the processing of the foodstuff is controlled using at least the information associated with the content property of the foodstuff and information indicative of the selected outcome.

8. The apparatus of claim 7 wherein the interface is arranged to communicate information indicative of the identified content property of the foodstuff and/or a progress of the processing of the foodstuff such as a change of the chromatic property.

9. The apparatus of claim 7 being arranged to transmit the information indicative of the content property and/or a progress of the processing of the foodstuff to a handheld unit.

10. The apparatus of claim 7 being arranged to receive an input that is indicative of the desired outcome from the handheld unit.

11. The apparatus of claim 7 comprising a memory for storing data indicative of a user profile, the user profile comprising information indicative of a desired outcome, wherein the interface is arranged to facilitate selection of a user profile and wherein the apparatus is arranged such that when a user profile is selected, the processing of the foodstuff is controlled using the information indicative of the desired outcome associated with the selected user profile and the information associated with the content property of the foodstuff.

12. The apparatus of claim 1 wherein the determined relation is a normalised difference that is defined as a difference of the information for one of the at least two wavelengths or wavelength ranges and the information for the other or another for the at least two wavelengths or wavelength ranges over a sum of the information for one of the at least two wavelengths or wavelength ranges and the information for the other or another for the at least two wavelengths or wavelength ranges.

13. The apparatus of claim 1 wherein the predetermined data comprises a plurality of predetermined relations, each predetermined relation being associated with at least one type of foodstuff.

14. The apparatus of claim 1 wherein the apparatus is arranged to compare the information for at least one of the at least two wavelengths or wavelength ranges with the predetermined data.

15. The apparatus of claim 1 wherein the source element is a heating source that is arranged to effect the change of chromatic property of the surface of the foodstuff.

16. The apparatus of claim 1 wherein the apparatus is further arranged to determine whether the foodstuff is present and, if it is determined that the foodstuff is not present, the apparatus is arranged to deactivate the element for processing of the foodstuff and/or generate an alert signal or internal trigger.

17. A handheld device for identifying a content property of foodstuff, the device comprising:

a light source for emitting light having at least two wavelengths or wavelength ranges; and a light detector arranged to generate an output indicative of a detected light intensity;

wherein, when light from the light source is directed to a surface of at least the foodstuff, at least a portion of light reflected from the surface of the foodstuff is detected by the detector and outputs are generated indicative of the detected light intensity by the detector, the device is arranged to determine, using a component processor, a relation between a generated output for one of the at least two wavelengths or wavelength ranges and a generated output for the other or another one of the at least two wavelengths or wavelength ranges, and wherein the device is further arranged to compare, using the component processor, the relation with predetermined data such that a content property of the foodstuff can be identified, and wherein information associated with the identified content property of the foodstuff is used for controlling an element for processing foodstuff, the element comprising a source element that is arranged to effect a change of a chromatic property of the surface of the foodstuff.

18. A method of identifying a content property of foodstuff, the method comprising the steps of:

providing the foodstuff having a surface;

illuminating the surface of the foodstuff with light having at least two wavelengths or wavelength ranges;

detecting at least a portion of light that is reflected and generating information indicative of an intensity of the detected reflected light for the at least two wavelength or wavelength ranges;

determining a relation between information for one of the at least two wavelengths or wavelength ranges and information for the other or another one of the at least two wavelengths or wavelength ranges;

comparing the determined relation to predetermined data such that a content property of the foodstuff can be identified;

processing the foodstuff; and controlling an element arranged for the processing of the foodstuff using at least information associated with the identified content property of the foodstuff, the element comprising a source element that is arranged to effect a change of a chromatic property of the surface of the foodstuff.

19. The apparatus of claim 1 comprising:

a component processor for identifying a content property of the foodstuff, the component processor being arranged to determine a relation between a generated output for one of the at least two wavelengths or wavelength ranges and a generated output for the other or another one of the at least two wavelengths or wavelength ranges and compare the determined relation with predetermined data such that the content property of the foodstuff can be identified; and a control processor for controlling the element for processing of the foodstuff using information associated with the identified content property of the foodstuff.

20. The apparatus of claim 1 comprising one processor for:

identifying a content property of the foodstuff, the component processor being arranged to determine a relation between a generated output for one of the at least two wavelengths or wavelength ranges and a generated output for the other or another one of the at least two wavelengths or wavelength ranges and compare the determined relation with predetermined data such that the content property of the foodstuff can be identified; and controlling the element for processing of the foodstuff using information associated with the identified content property of the foodstuff.

* * * * *